US00PP35031P2

(12) United States Plant Patent
Worthy

(10) Patent No.: US PP35,031 P2
(45) Date of Patent: Mar. 14, 2023

(54) ***RED MAPLE* TREE NAMED 'RVF-1'**

(50) Latin Name: *Red Maple rubrum*
Varietal Denomination: 'RVF-1'

(71) Applicant: Jeremy Brantley Worthy, McDonough, GA (US)

(72) Inventor: Jeremy Brantley Worthy, McDonough, GA (US)

(73) Assignee: RENFROE VALLEY FARMS LLC, McDonough, GA (US)

( * ) Notice: Subject to any disclaimer, the term of this patent is extended or adjusted under 35 U.S.C. 154(b) by 0 days.

(21) Appl. No.: 17/724,553

(22) Filed: Apr. 20, 2022

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./216, 224
See application file for complete search history.

*Primary Examiner* — Susan McCormick Ewoldt
(74) *Attorney, Agent, or Firm* — Penny J. Aguirre

(57) ABSTRACT

A new cultivar of *Acer* tree named 'RVF-1' that is characterized by its fast growth rate. Its consistent fall foliage colors that is grey-red in color in early November, its foliage with good resistance to diseases and pests, and its high tolerance to extreme heat and humidity.

3 Drawing Sheets

Botanical classification: *Red Maple rubrum.*
Variety denomination: 'RVF-1'.

BACKGROUND OF THE INVENTION

The present invention relates to a new and distinct cultivar of *Acer* tree, botanically known as *Acer rubrum* 'RVF-1' and will be referred to hereinafter by its cultivar name, 'RVF-1'. The new cultivar of *Acer* is a deciduous tree grown for use as a landscape plant.

The Inventor discovered the new cultivar 'RVF-1' in a container in a production block of *Acer rubrum* 'October Glory' (U.S. Plant Pat. No. 2,116) in McDonough, Ga. in the fall of 2015. As the containers had been planted with liners from vegetatively propagated plants of 'October Glory', the new cultivar is presumed to be a branch mutation of 'October Glory'. 'RVF-1' was found to be unique by DNA testing compared to all varieties in production at the liner source nursery and other known cultivars and varieties of *Acer rubrum* in the trade.

Asexual propagation of the new cultivar was first accomplished by semi-hardwood stem cuttings in summer of 2018 by the Inventor in Ft. Valley, Ga. Asexual propagation by semi-hardwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'RVF-1' as a unique cultivar of *Acer.*

1. 'RVF-1' exhibits a fast growth rate.
2. 'RVF-1' exhibits consistent fall foliage colors that is grey-red in color in early November.
3. 'RVF-1' exhibits foliage with good resistance to diseases and pests.

4. 'RVF-1' exhibits a high tolerance to extreme heat and humidity.

The parent plant of 'RVF-1'. 'October Glory', is similar to 'RVF-1' in having foliage that is green in color and glossy in texture. 'October Glory' differs from 'RVF-1' in having a broader canopy, leaves that are smaller in size, petioles that are shorter in length, summer foliage that is lighter green in color, and fall foliage that is lighter red in color. 'RVF-1' can be compared to the *Acer rubrum* cultivar 'Brandywine' (not patented). 'Brandywine' is similar to 'RVF-1' in having foliage that is dark red in color. 'Brandywine' differs from 'RVF-1' in having a broader canopy, leaves that are smaller in size, petioles that are shorter in length, and a faster plant growth rate.

BRIEF DESCRIPTION OF THE DRAWINGS

The accompanying color photographs illustrate the overall appearance and distinct characteristics of the new *Acer*. The photographs in FIG. 1 and FIG. 2 were taken of a 6-year-old parent tree 'RVF-1' in the ground in McDonough, Ga.

The photograph in FIG. 1 provides an overall view of the foliage and plant habit of 'RFV-1' in summer.

Figure 1:
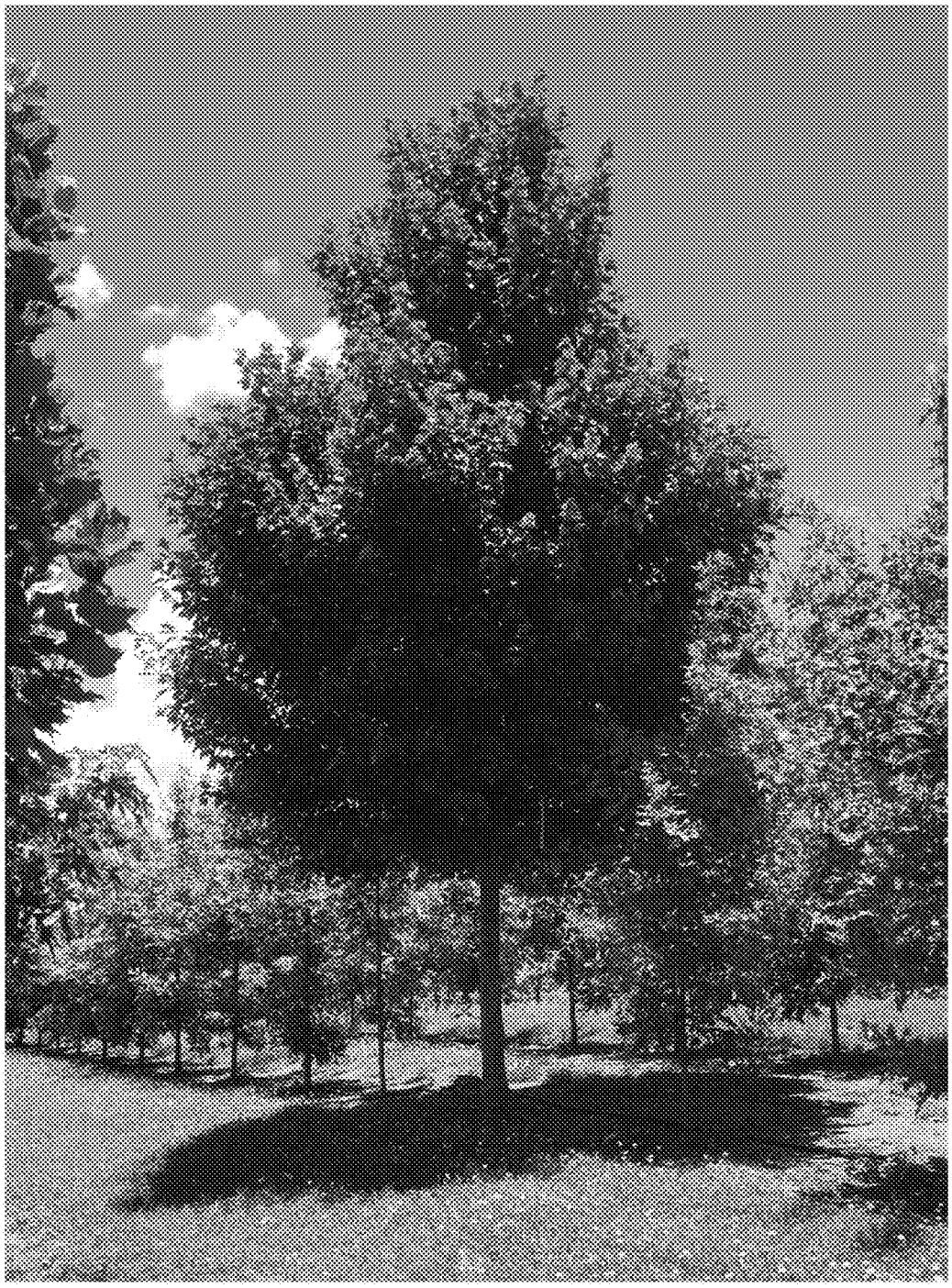
Figure 2:
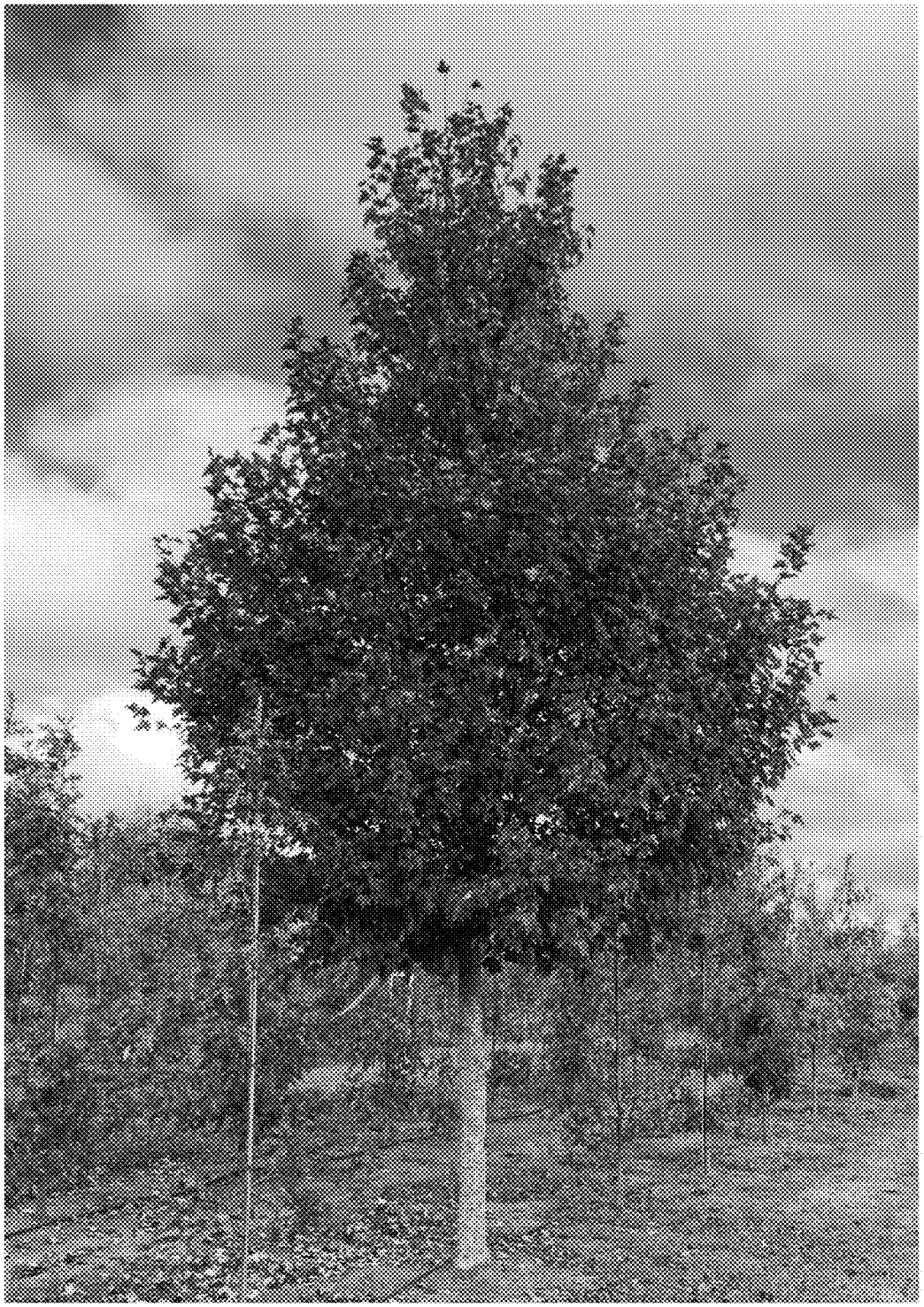

The photograph in FIG. 2 provides an overall view of the foliage and plant habit of 'RFV-1' in fall.

Figure 3:
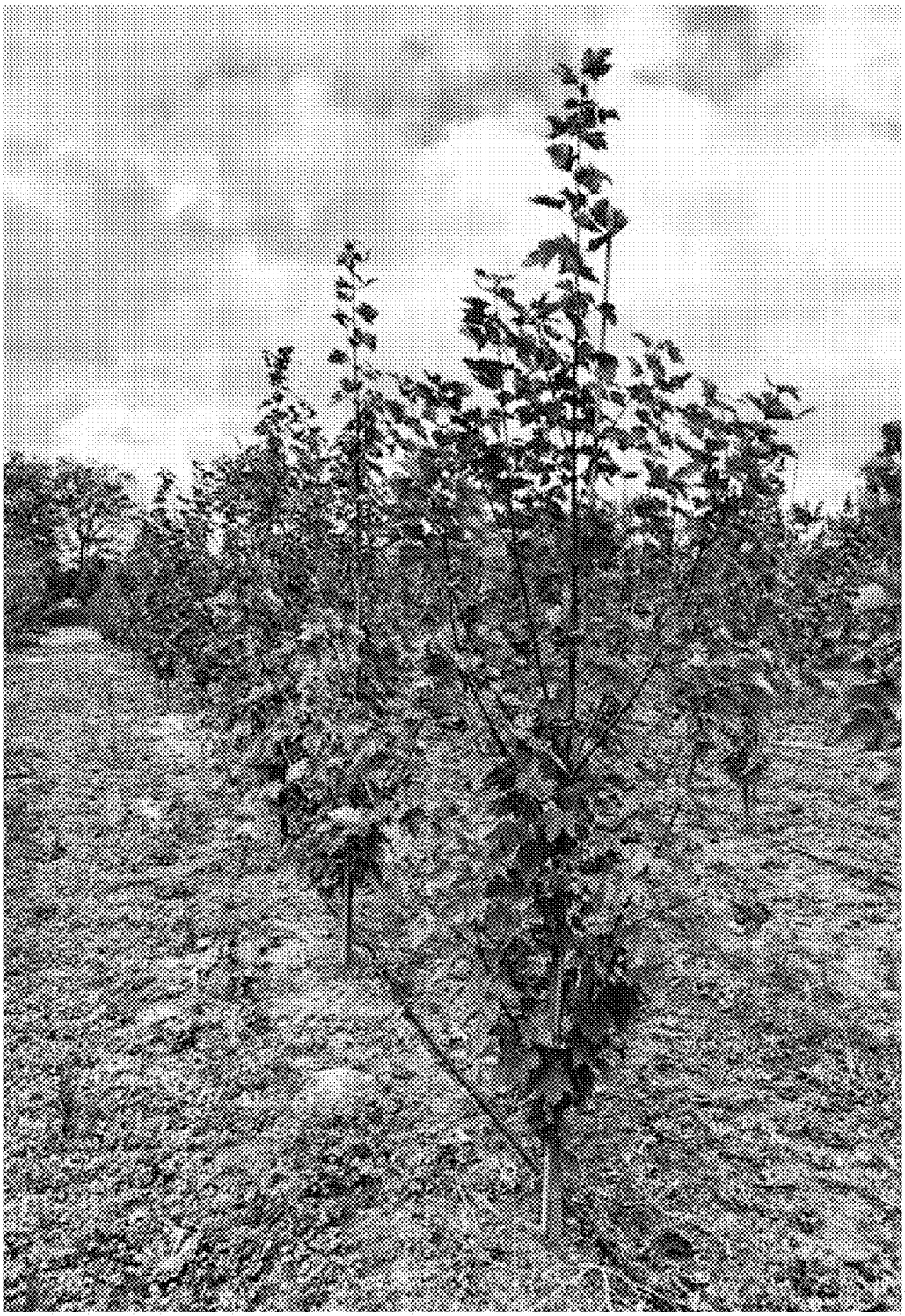

The photograph in FIG. 3 provides a view of a row of 3-year-old plants of 'RFV-1' in fall in Barnesville, Ga.

The colors in the photographs may differ slightly from the color values cited in the detailed botanical description, which accurately describe the colors of the new *Acer.*

DETAILED BOTANICAL DESCRIPTION

The following is a detailed description of a six-year-old parent and three-year-old offspring of the new cultivar as observed outdoors in field production in McDonough, Ga. and Barnesville, Georgia. The phenotype of the new cultivar may vary with variations in environmental, climatic, and cultural conditions, as it has not been tested under all possible environmental conditions. The color determination is in accordance with the 2001 of The Colour Chart of The Royal Horticultural Society, London, England, except where general color terms of ordinary dictionary significance are used.

General description:

*Blooming period*.—Blooms 3 to 4 weeks from mid to late March in Georgia.

*Plant type*.—Deciduous tree.

*Plant habit*.—Upright oval with strong central leader.

*Height and spread*.—Reaches an average of 6.7 m in height and 3.65 m in width as a 6-year-old plant with a caliper of 14.6 cm when measured 30.5 cm above ground.

*Hardiness*.—At least in U.S.D.A. Zones 6 to 8.

*Diseases and pests*.—Good resistance to rot and cankers caused by *Botryospoheria* sp. and to Tip Borer (*Proteoterus aesculana*), Leaf Hopper (carries the bacterium *Xylella fastidiosa*) and Ambrosia Beetle (*Xylosandrus germanus* or *Xylosandrus crassiusculus*).

*Root description*.—Fibrous roots, freely branched.

*Propagation*.—Semi-hardwood stem cuttings.

*Root development*.—Roots initiate in 32 days and a fully rooted young plant is produced in 5 to 7 months.

*Growth habit*.—Vigorous in comparison to most cultivars of *Acer rubrum*.

Branch description:

*Branch shape*.—Round.

*Stem color*.—Young stems; 145A with 183A, older stems 145A and 199C, trunk; 198A with striations of 198B.

*Branch size*.—Main stems; 1.6 m in length, 7.6 cm in width, trunk; 14.6 cm when measured 30.5 cm above ground.

*Internode length*.—Highly variable.

*Stem surface*.—Branches smooth, trunk moderately ridged.

*Branching habit*.—Radiating outward and slightly curved upward, held in an average angle of 65°.

Foliage description:

*Leaf shape*.—Broadly ovate to lanceolate in overall outline.

*Leaf division*.—Simple.

*Leaf base*.—Hastate.

*Leaf apex*.—Acuminate.

*Leaf venation*.—Pinnate, 163C on upper surface and 160C on lower surface on mature summer foliage.

*Leaf margins*.—Primarily tri-lobed, lobe margins serrated to slightly lobed.

*Leaf arrangement*.—Opposite.

*Leaf surface* (*upper and lower surface*).—Glabrous.

*Leaf color*.—Newly expanded leaves in summer; upper surface 137C, lower surface 137D, mature foliage; upper surface 137A, lower surface 138A, fall foliage; upper and lower surface; becoming increasingly suffused with N77A with cool temperatures with some tips on newer growth 60B to 60C, leaves with full sun exposure N77A.

*Leaf size*.—Up to 9 cm in length and 7 cm width, lobes; center lobe up to 7.5 cm in length and 4 cm in width, side basal lobes up to 4 cm in length and 1.8 cm in width.

*Leaf attachment*.—Petiolate.

*Petioles*.—Up of 4.5 cm in length and 1.5 mm in width, held horizontal and slightly drooping to about a 45° angle upward from branch, color 183B on upper surface and 160C on lower surface.

*Stipules*.—None.

Inflorescence description:

*Inflorescence type*.—Flowers solitary, terminal.

*Flowers* (*female only*).—Pistillate, small in size, sessile, umbel, 5 to 6 flowers, held tightly and surrounded by bud scales, with the flower cluster appearing oval to urn shaped with flaring styles.

*Flower buds*.—Ovoid in shape, 3 mm in length, 2 mm in width, glabrous surface, 145C in color.

*Sepals and petals*.—5 each, rotate, ovate in shape, rounded in shape, 1 mm in height and width, 53A in color, indistinguishable between sepals and petals.

Reproductive organs:

*Pistils*.—1 to 2 mm in length, 185A in color.

*Stigmas*.—2 to 3 mm in length, 0.05 mm in width, 185A in color.

*Stamens*.—Non-functional, 1 mm in length, 0.5 mm in width.

*Fruit and seed*.—Samaras are 2-winged, 145C in color and heavily suffused with 53A, an average of 1.2 cm in length and 4 mm in width held in pairs by a pedicel in clusters of up to 5.

It is claimed:

1. A new and distinct variety of *Acer* tree named 'RVF-1' as described and illustrated herein.

* * * * *